United States Patent
Vendely et al.

(10) Patent No.: US 11,166,725 B2
(45) Date of Patent: Nov. 9, 2021

(54) CONFIGURATION OF BUTTRESS FOR SURGICAL STAPLER

(71) Applicant: Ethicon LLC, Guaynabo, PR (US)

(72) Inventors: Michael J. Vendely, Lebanon, OH (US); Trevor J. Barton, Cincinnati, OH (US); David T. Krumanaker, Cincinnati, OH (US); Pamela M. Ridgley, Lebanon, OH (US); Emily A. Schellin, Cincinnati, OH (US); Rebecca Spatholt, Cincinnati, OH (US); Heather Strang, West Chester, OH (US)

(73) Assignee: Cilag GmbH International, Zug (CH)

(*) Notice: Subject to any disclaimer, the term of this patent is extended or adjusted under 35 U.S.C. 154(b) by 244 days.

(21) Appl. No.: 16/235,488

(22) Filed: Dec. 28, 2018

(65) Prior Publication Data

US 2020/0205821 A1 Jul. 2, 2020

(51) Int. Cl.
| A61B 17/068 | (2006.01) |
| A61B 17/072 | (2006.01) |
| A61B 17/00  | (2006.01) |

(52) U.S. Cl.
CPC ............ *A61B 17/07292* (2013.01); *A61B 2017/00951* (2013.01); *A61B 2017/07264* (2013.01); *A61B 2017/07271* (2013.01)

(58) Field of Classification Search
CPC .......... A61B 17/07207; A61B 17/072; A61B 17/07292; A61B 17/115–17/1157;
(Continued)

(56) References Cited

U.S. PATENT DOCUMENTS

| 4,805,823 A | 2/1989 | Rothfuss |
| 5,415,334 A | 5/1995 | Williamson, IV et al. |

(Continued)

FOREIGN PATENT DOCUMENTS

| EP | 1520525 A1 | 4/2005 |
| EP | 2786718 A2 | 10/2014 |

(Continued)

OTHER PUBLICATIONS

U.S. Appl. No. 16/234,727, entitled "Surgical Stapler with Tissue Engagement Features Around Tissue Containment Pin," filed Dec. 28, 2018.

(Continued)

*Primary Examiner* — Kathleen S Holwerda
(74) *Attorney, Agent, or Firm* — Frost Brown Todd LLC

(57) ABSTRACT

A surgical system and related methods includes a buttress applier cartridge, a first buttress assembly, and a second buttress assembly. The buttress applier cartridge has a housing and a platform. The first and second buttress assemblies respectively includes first and second buttresses and first and second adhesive layers thereon. The first adhesive layer is parallel to the first buttress and defines a first adhesive pattern having a first outer adhesive profile. The second adhesive layer is parallel to the second buttress and defines a second adhesive pattern having a second outer adhesive profile. The exposed second outer adhesive profile in the transverse direction is the same as the exposed first outer adhesive profile in an opposite transverse direction such that the first and second buttress assemblies are interchangeable with the first and second portions of the end effector of the surgical instrument.

20 Claims, 9 Drawing Sheets

(58) Field of Classification Search
CPC ........... A61B 2017/07221–2017/07285; A61B 2017/00951
See application file for complete search history.

(56) References Cited

U.S. PATENT DOCUMENTS

| | | | |
|---|---|---|---|
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 6,978,921 B2 | 12/2005 | Shelton, IV et al. |
| 6,988,650 B2 | 1/2006 | Schwemberger et al. |
| 7,000,818 B2 | 2/2006 | Shelton, IV et al. |
| 7,134,587 B2 | 11/2006 | Schwemberger et al. |
| 7,143,923 B2 | 12/2006 | Shelton, IV et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,524,320 B2 | 4/2009 | Tierney et al. |
| 7,644,848 B2 | 1/2010 | Swayze et al. |
| 7,691,098 B2 | 4/2010 | Wallace et al. |
| 7,721,930 B2 | 5/2010 | McKenna et al. |
| 7,806,891 B2 | 10/2010 | Nowlin et al. |
| 8,141,762 B2 | 3/2012 | Bedi et al. |
| 8,210,411 B2 | 7/2012 | Yates et al. |
| 8,371,491 B2 | 2/2013 | Huitema et al. |
| 8,408,439 B2 | 4/2013 | Huang et al. |
| 8,453,914 B2 | 6/2013 | Laurent et al. |
| 8,479,969 B2 | 7/2013 | Shelton, Iv |
| 8,573,461 B2 | 11/2013 | Shelton, Iv et al. |
| 8,573,465 B2 | 11/2013 | Shelton, IV |
| 8,579,990 B2 | 11/2013 | Priewe |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,800,838 B2 | 8/2014 | Shelton, IV |
| 8,801,735 B2 | 8/2014 | Shelton, IV et al. |
| 8,814,025 B2 | 8/2014 | Miller et al. |
| 8,820,605 B2 | 9/2014 | Shelton, IV |
| 8,844,789 B2 | 9/2014 | Shelton, IV et al. |
| 8,899,464 B2 | 12/2014 | Hueil et al. |
| 8,992,060 B2 | 4/2015 | Dassanayake et al. |
| 8,998,060 B2 | 4/2015 | Bruewer et al. |
| 9,101,359 B2 | 8/2015 | Smith et al. |
| 9,186,142 B2 | 11/2015 | Fanelli et al. |
| 9,198,644 B2 | 12/2015 | Balek et al. |
| 9,211,120 B2 | 12/2015 | Scheib et al. |
| 9,301,759 B2 | 4/2016 | Spivey et al. |
| 9,393,018 B2 | 7/2016 | Wang et al. |
| 9,398,911 B2 | 7/2016 | Auld et al. |
| 9,492,170 B2 | 11/2016 | Bear et al. |
| 9,517,065 B2 | 12/2016 | Simms et al. |
| 9,597,082 B2 | 3/2017 | Stokes et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 9,848,871 B2 | 12/2017 | Harris et al. |
| 9,867,615 B2 | 1/2018 | Fanelli et al. |
| 9,913,642 B2 | 3/2018 | Leimbach et al. |
| 9,936,954 B2 | 4/2018 | Shelton, IV et al. |
| 9,999,408 B2 | 6/2018 | Boudreaux et al. |
| 10,045,780 B2 | 8/2018 | Adams et al. |
| 10,092,292 B2 | 10/2018 | Boudreaux et al. |
| D833,010 S | 11/2018 | Harris et al. |
| 10,123,798 B2 | 11/2018 | Baxter, III et al. |
| D836,198 S | 12/2018 | Harris et al. |
| D836,199 S | 12/2018 | Schowalter et al. |
| 10,349,939 B2 | 7/2019 | Shelton, IV et al. |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2008/0169328 A1 | 7/2008 | Shelton |
| 2012/0241493 A1 | 9/2012 | Baxter, III et al. |
| 2013/0068816 A1 | 3/2013 | Vasudevan et al. |
| 2013/0075447 A1 | 3/2013 | Weisenburgh et al. |
| 2013/0146643 A1* | 6/2013 | Schmid ............. A61B 17/0643 227/180.1 |
| 2013/0206813 A1 | 8/2013 | Nalagatla |
| 2014/0239037 A1 | 8/2014 | Boudreaux et al. |
| 2015/0351758 A1 | 12/2015 | Shelton, IV et al. |
| 2016/0089146 A1 | 3/2016 | Harris et al. |
| 2016/0278774 A1* | 9/2016 | Shelton, IV ..... A61B 17/07292 |
| 2017/0027571 A1 | 2/2017 | Nalagatla et al. |
| 2017/0049444 A1 | 2/2017 | Schellin et al. |
| 2017/0055980 A1 | 3/2017 | Vendely et al. |
| 2017/0055981 A1* | 3/2017 | Vendely ........... A61B 17/07292 |
| 2017/0055982 A1 | 3/2017 | Zeiner et al. |
| 2017/0055986 A1 | 3/2017 | Harris et al. |
| 2017/0056016 A1 | 3/2017 | Barton et al. |
| 2017/0056017 A1 | 3/2017 | Vendely et al. |
| 2017/0056018 A1 | 3/2017 | Zeiner et al. |
| 2017/0086823 A1 | 3/2017 | Leimbach et al. |
| 2017/0086837 A1 | 3/2017 | Vendely et al. |
| 2017/0086842 A1 | 3/2017 | Shelton, IV et al. |
| 2018/0235610 A1 | 8/2018 | Harris et al. |
| 2018/0235611 A1 | 8/2018 | Harris et al. |
| 2018/0235619 A1 | 8/2018 | Harris et al. |
| 2018/0235626 A1 | 8/2018 | Shelton, IV et al. |
| 2018/0250001 A1 | 9/2018 | Aronhalt et al. |
| 2019/0000481 A1 | 1/2019 | Harris et al. |

FOREIGN PATENT DOCUMENTS

| | | |
|---|---|---|
| EP | 3072459 A1 | 9/2016 |
| WO | WO 1998/017180 A1 | 4/1998 |

OTHER PUBLICATIONS

U.S. Appl. No. 16/234,740, entitled "Surgical Stapler with Sloped Staple Deck for Varying Tissue Compression," filed Dec. 28, 2018.
U.S. Appl. No. 16/235,473, entitled "Adhesive Distribution on Buttress for Surgical Stapler," filed Dec. 28, 2018.
U.S. Appl. No. 16/235,503, entitled "Surgical Stapler Buttress with Tissue In-Growth Promotion," filed Dec. 28, 2018.
U.S. Appl. No. 16/235,522, entitled "Applicator for Surgical Stapler Buttress," filed Dec. 28, 2018.
U.S. Appl. No. 16/235,541, entitled "Packaging for Surgical Stapler Buttress," filed Dec. 28, 2018.
U.S. Appl. No. 16/235,617, entitled "Method of Applying Buttresses to Surgically Cut and Stapled Sites," filed Dec. 28, 2018.
U.S. Appl. No. 16/235,630, entitled "Curved Tip Surgical Buttress Applicator with Opening Feature for Curved Tip Alignment," filed Dec. 28, 2018.
U.S. Appl. No. 16/235,670, entitled "Curved Tip Surgical Buttress Assembly Applicator with Proximal Alignment Features," filed Dec. 28, 2018.
U.S. Appl. No. 16/235,681, entitled "Curved Tip Surgical Buttress Assembly Applicator with Compression Layer Pocket Features," filed Dec. 28, 2018.
Design U.S. Appl. No. 29/675,045, entitled "Surgical Stapler Deck with Tissue Engagement Cleat Features," filed Dec. 28, 2018.
Design U.S. Appl. No. 29/675,047, entitled "Surgical Stapler Deck with Tissue Engagement Recess Features," filed Dec. 28, 2018.

(56) References Cited

OTHER PUBLICATIONS

Design U.S. Appl. No. 29/675,168, entitled "Applicator for Surgical Stapler Buttress," filed Dec. 28, 2018.
Design U.S. Appl. No. 29/675,170, entitled "Buttress for Surgical Stapler," filed Dec. 28, 2018.
Design U.S. Appl. No. 29/675,172, entitled "Tray for Surgical Stapler Buttress Applicator," filed Dec. 28, 2018.
Design U.S. Appl. No. 29/675,197, entitled "Applicator for a Stapler Buttress," filed Dec. 28, 2018.
Design U.S. Appl. No. 29/675,199, entitled "Buttress Assembly for a Surgical Stapler," filed Dec. 28, 2018.
U.S. Appl. No. 62/209,041, entitled "Method and Apparatus for Applying a Buttress to End Effector of a Surgical Stapler," filed Aug. 24, 2015.
Partial European Search Report dated Mar. 16, 2020, for Application No. 19219529.5, 16 pages.
Extended European Search Report and Written Opinion dated Jul. 10, 2020, for Application No. 19219529.5, 19 pages.
International Search Report and Written Opinion dated May 13, 2020, for International Application No. PCT/IB2019/060819, 21 pages.

* cited by examiner

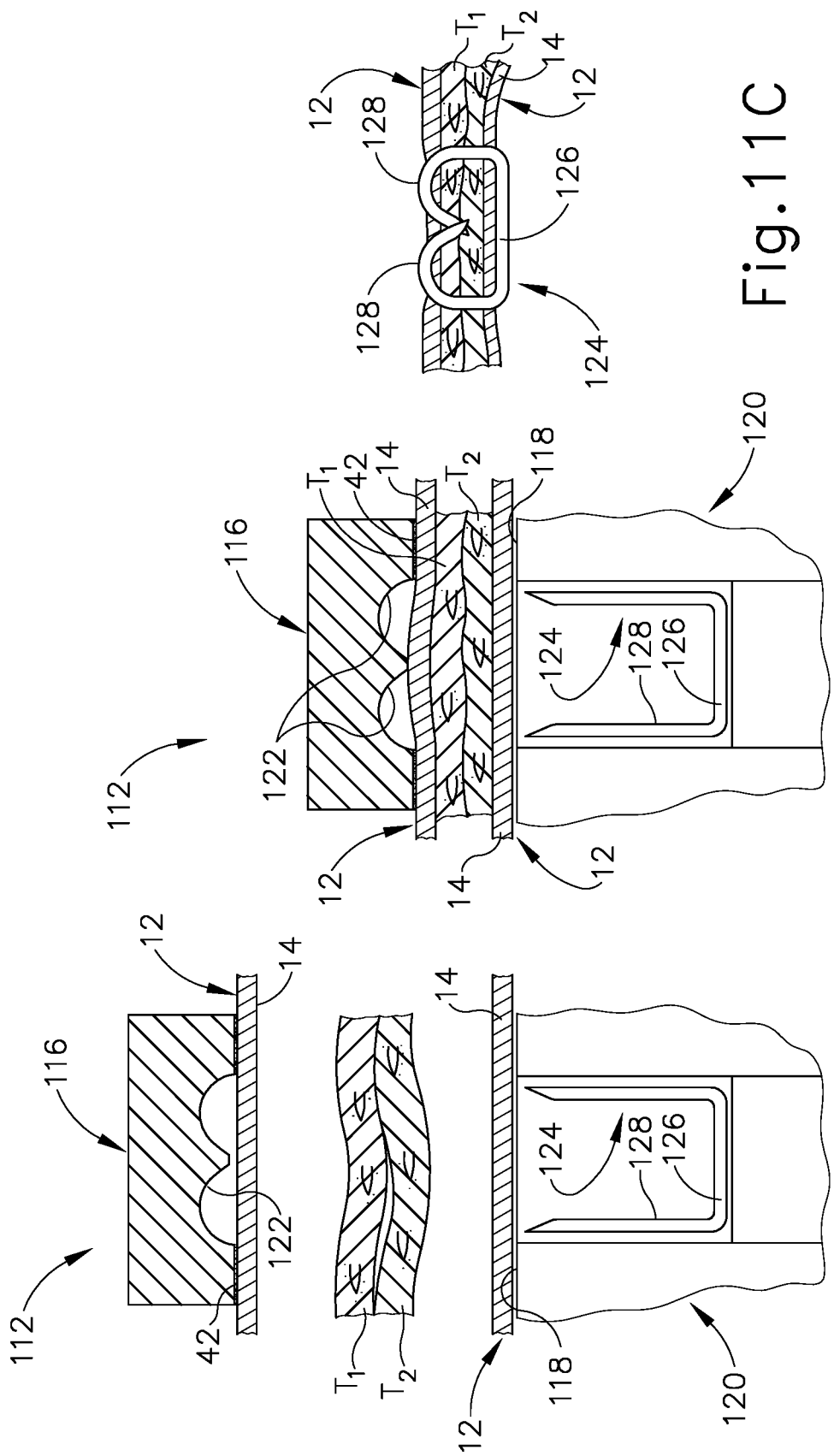

CONFIGURATION OF BUTTRESS FOR SURGICAL STAPLER

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Pat. No. 9,186,142, entitled "Surgical Instrument End Effector Articulation Drive with Pinion and Opposing Racks," issued Nov. 17, 2015; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,839,421, entitled "Jaw Closure Feature for End Effector of Surgical Instrument," issued Dec. 12, 2017; U.S. Pat. No. 9,867,615, entitled "Surgical Instrument with Articulation Lock having a Detenting Binary Spring," issued Jan. 16, 2018; U.S. Pat. No. 9,622,746, entitled "Distal Tip Features for End Effector of Surgical Instrument," issued Apr. 18, 2017; U.S. Patent Pub. No. 2014/0239037, entitled "Staple Forming Features for Surgical Stapling Instrument," published Aug. 28, 2014; U.S. Pat. No. 9,795,379, entitled "Surgical Instrument with Multi-Diameter Shaft," issued Oct. 24, 2017; and U.S. Pat. No. 9,808,248, entitled "Installation Features for Surgical Instrument End Effector Cartridge," issued Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pat. No. 9,597,082, entitled "Method and Apparatus for Sealing End-to-End Anastomosis" Mar. 21, 2017; U.S. Pat. No. 9,398,911, entitled "Rotary Powered Surgical Instruments with Multiple Degrees of Freedom," issued Jul. 26, 2016; U.S. Pub. No. 2013/0206813, entitled "Linear Stapler," published Aug. 15, 2013; U.S. Pub. No. 2008/0169328, entitled "Buttress Material for Use with a Surgical Stapler," published Jul. 17, 2008; U.S. Pat. No. 9,848,871, entitled "Woven and Fibrous Materials for Reinforcing a Staple Line," issued Dec. 26, 2017; U.S. Pat. No. 9,936,954, entitled "Devices and Methods for Sealing Staples in Tissue," issued Apr. 10, 2018; and U.S. Pat. Pub. No. 2016/0089146, entitled "Radically Expandable Staple Line" published Mar. 31, 2016. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples. Such buttress material may be applied to the surgical stapling instrument with a buttress applier cartridge. The buttress applier cartridge retains the buttress material prior to application and releases the buttress material once applied to the surgical stapling instrument. An example of such buttress applier cartridge is disclosed in U.S. Pat. Pub. No. 2017/0056016, entitled "Surgical Stapler Buttress Applicator with End Effector Actuated Release Mechanism," published Mar. 2, 2017, the disclosure of which is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 11A depicts a sectional side view of a portion of the end effector of FIG. 10B with the buttress assemblies of FIG. 1 applied to the end effector and tissue positioned between the buttress assemblies with the upper and lower jaws in the open position;

FIG. 11B depicts the sectional side view of the portion of the end effector and the buttress assemblies similar to FIG. 11A, but showing the upper and lower jaws in the closed position;

FIG. 11C depicts the sectional side view of the buttress assemblies similar to FIG. 11B, but showing the buttress assemblies secured to the tissue with a staple formed in the tissue;

Figure 1:
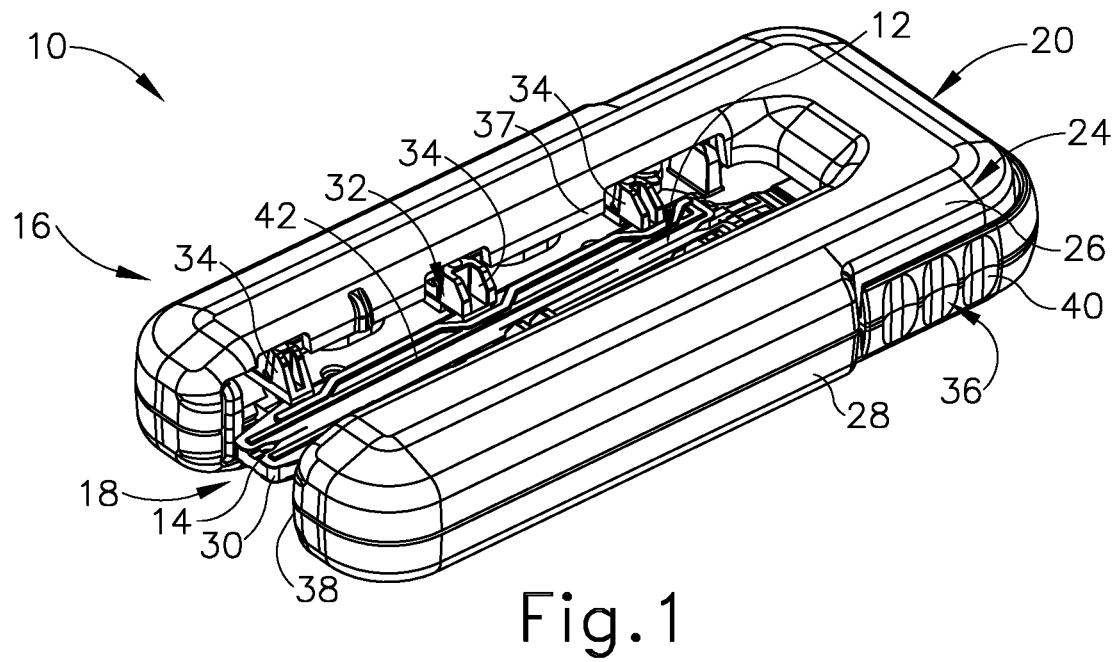
FIG. 1 depicts a perspective view of an exemplary buttress applier cartridge assembly that includes an example of a buttress applier cartridge carrying an example of a buttress assembly for an upper jaw and an example of another buttress assembly for a lower jaw.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It should be understood that terms such as "proximal" and "distal" are used herein with reference to a clinician gripping a surgical instrument, such as surgical and severing instrument (110) and buttress applier cartridge assembly (10) discussed below. It will be further appreciated that for convenience and clarity, spatial terms such as "upright,"

"upside-down," "upper," "lower," "bottom," and "top" are used herein with respect to the drawings. However, surgical instruments are used in many orientations and positions, and these terms are not intended to be limiting and absolute.

I. Exemplary Buttress Applier Cartridge Assembly

In some instances, it may be desirable to use an exemplary buttress applier cartridge assembly (10) as shown in FIG. 1 to equip a surgical instrument with a buttress assembly (12) for forming staples in tissue with a buttress (14). Such buttress (14) inhibits the formed staples from pulling through the tissue to thereby reduce a risk of tissue tearing at or near the site of formed staples. In addition to or as an alternative to providing structural support and integrity to a line of staples, buttress (14) may provide various other kinds of effects such as spacing or gap-filling, administration of therapeutic agents, and/or other effects. Prior to use with the surgical instrument, one or more buttresses (14) is releasably retained on a buttress applier cartridge (16), which is configured to deposit buttress assembly (10) onto surgical instrument for use as discussed below in more detail in an exemplary surgical instrument (18) (see FIG. 10A).

Additional features may be combined as applicable with the following example of buttress applier cartridge assembly (10). Such features are described in U.S. patent application Ser. No. 16/235,473, entitled "Adhesive Distribution on Buttress for Surgical Stapler," filed on Dec. 28, 2018, published as U.S. Pub. No. 2020/0205820 on Jul. 2, 2020; U.S. patent application Ser. No. 16/235,503,entitled "Surgical Stapler Buttress with Tissue In-Growth Promotion," filed on Dec. 28, 2018, published as U.S. Pub. No. 2020/0205822 on Jul. 2, 2020; U.S. patent application Ser. No. 16/235,522, entitled "Applicator for Surgical Stapler Buttress," filed on, Dec. 28, 2018, issued as U.S. Pat. No. 11,116,505 on Sep. 14, 2021; U.S. pat. app. Ser. No. 16,235,541, entitled "Packaging for Surgical Stapler Buttress," filed on Dec. 28, 2018,published as U.S. Pub. No. 2020/0205824 on Jul. 2, 2020; U.S. patent application Ser. No. 16/235,617, entitled "Method of Applying Buttresses to Surgically Cut and Stapled Sites," filed on Dec. 28, 2018, issued as U.S. Pat. No. 11,033,269 on Jul. 15, 2021; U.S. patent application Ser. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020; U.S. patent application Ser. No. 16/235,670, entitled "Curved Tip Surgical Stapler Buttress Assembly Applicator with Proximal Alignment Features," filed on Dec. 28, 2018, issued as U.S. Pat. No. 10,905,424 on Feb. 2, 2021; and U.S. patent application Ser. No. 16/235,681 entitled "Curved Tip Surgical Stapler Buttress Assembly Applicator with Compression Layer Pocket Feature," filed on Dec. 28, 2018, issued as U.S. Pat. No. 11,103,243 on Aug. 21, 2021; U.S. patent application Ser. No. 29/675,168, entitled "Applicator for a Surgical Stapler Buttress," filed on Dec. 28, 2018, issued as U.S. Pat. No. D901,686 on Nov. 10, 2020; U.S. patent application Ser. No. 29/675,170, entitled "Buttress for Surgical Stapler," filed on Dec. 28, 2018; U.S. patent application Ser. No. 29/675,172, entitled "Tray for Surgical Stapler Buttress Applicator," filed on Dec. 28, 2018, issued as U.S. Pat No. D922,576 on Jun. 15, 2021; U.S. patent application Ser. No. 29/675,197, entitled "Applicator for a Surgical Stapler Buttress," filed on Dec. 28, 2018, issued as U.S. Pat. No. D903,115 on Nov. 24, 2020; and U.S. patent application Ser. No. 29/675,199, entitled "Buttress Assembly for a Surgical Stapler," filed on Dec. 28, 2018, the disclosures of which are hereby incorporated by reference.

A. Exemplary Buttress Applier Cartridge

Figure 2:
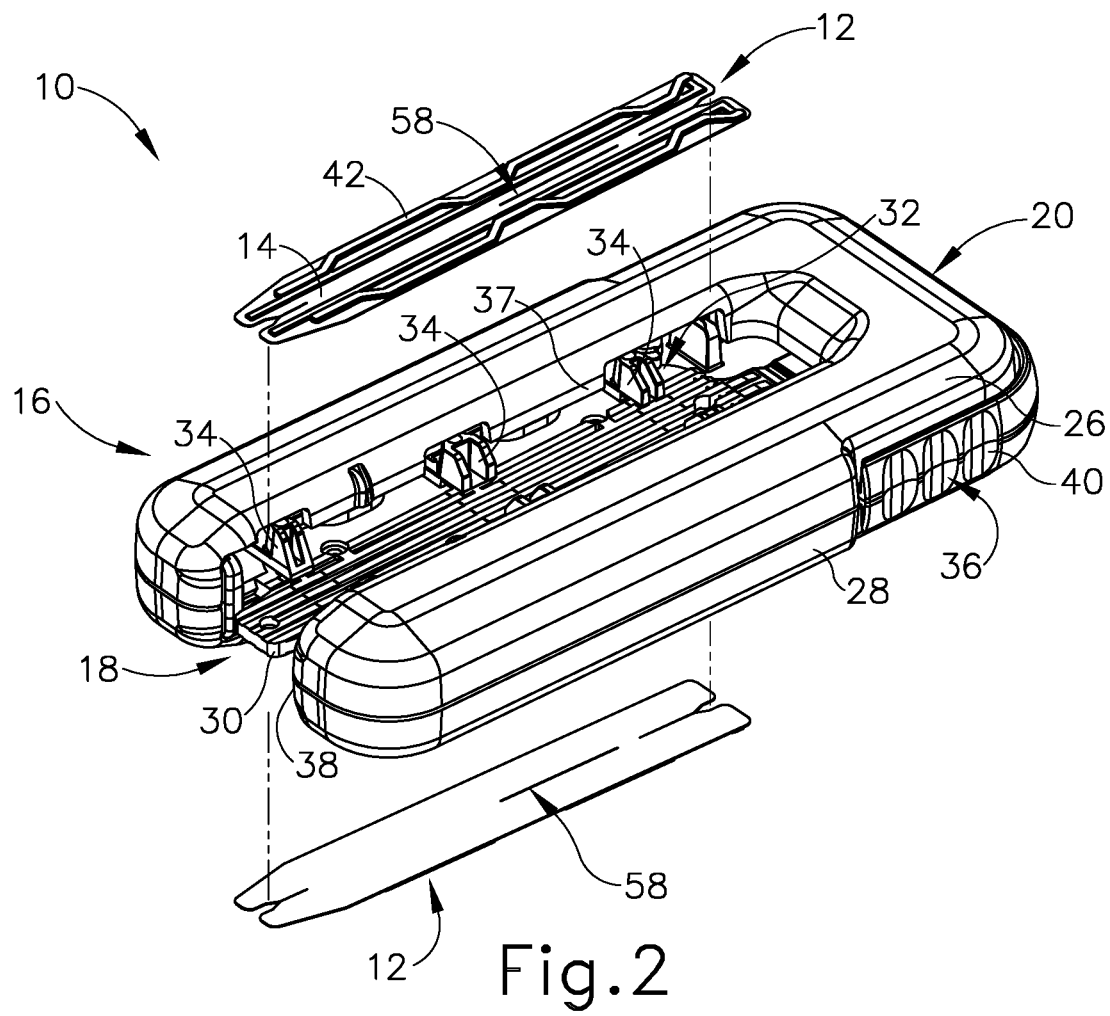
FIG. 2 depicts a partially exploded perspective view of the buttress applier cartridge assembly of FIG. 1 showing the buttress assemblies removed from the buttress applier cartridge.
Figure 10A:
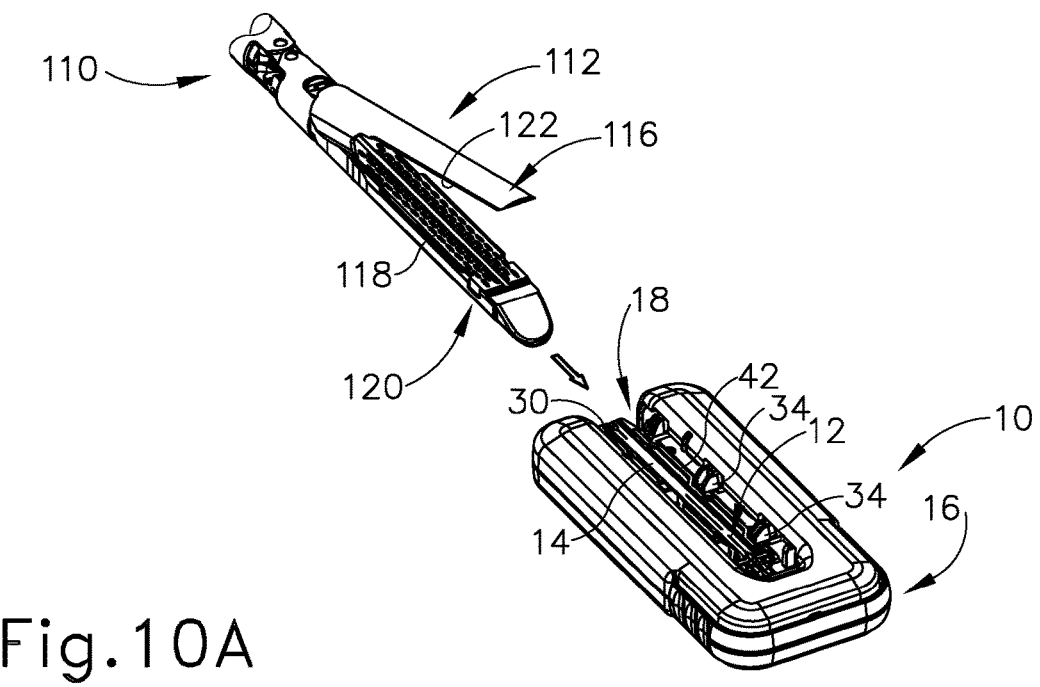
FIG. 10A depicts a perspective view of an end effector of an exemplary surgical instrument showing the buttress applier cartridge assembly of FIG. 1 approaching the end effector with the upper and lower jaws in an open position.

FIGS. 1-2 show buttress applier cartridge assembly (10) including a pair of buttress assemblies (12) releasably retained on buttress applier cartridge (16), which supports and protects buttress assemblies (12) prior to use and further aids with loading buttress assemblies (12) on surgical instrument (110) (see FIG. 10A). Buttress applier cartridge (16) of the present example includes an open end (18) and a closed end (20). Open end (18) is configured to receive end effector (112) (see FIG. 10A) as described below in greater detail. Buttress applier cartridge (16) further includes a housing assembly (24) having an upper housing (26) and a lower housing (28), which each generally define a "U" shape to present open end (18). Various components are interposed between upper and lower housings (26, 28). In particular, these components include a platform (30), a pair of actuator sleds (32) having arms (34), and a chassis (36).

Platform (30) of the present example supports upper buttress assembly (12) on one side of platform (30) and lower buttress assembly (12) on the other side of platform (30). Platform (30) is exposed in recesses that are formed between the prongs of the "U" configuration of upper and lower housings (26, 28). Thus, upper housing (26) has an upper gap (37) extending to the open end (18) along an upper surface of platform (30), and lower housing (28) similarly has a lower gap (38) extending to the open end (18) along the lower surface of platform (30). The location of platform (30) and buttress assemblies (12) in such recesses may prevent inadvertent contact between buttress assemblies (12) and other devices in the operating room. In other words, upper and lower housings (26, 28) may provide some degree of physical shielding of buttress assemblies (12).

In the present example, the outer edges of platform (30) are captured between upper and lower housings (26, 28) and include retention features (not shown) that further engage upper and lower housings (26, 28) to prevent platform (30) from sliding relative to upper and lower housings (26, 28). In some versions, platform (30) is formed of a material that provides a high coefficient of friction, thereby reducing any tendency that buttress assemblies (12) might otherwise have to slide along corresponding surfaces of platform (30). For instance, platform (30) may comprise an elastomeric material and/or a foam material. In some instances, platform (30) is formed of a compressible foam material that is configured to maintain a compressed configuration after being compressed by end effector (112) (see FIG. 10A). By way of example only, platform (30) may comprise Santoprene, closed-cell polyurethane foam, any other compressible material, and/or a material that may be made compressible via geometry (e.g., a rubber material with deformable standing features). Various suitable materials and structural configurations that may be used to form platform (30) will be apparent to those of ordinary skill in the art in view of the teachings herein.

Chassis (36) is configured to cooperate with upper and lower housings (26, 28) to provide a mechanical ground for moving components of buttress applier cartridge (16) and provide structural support for components of buttress applier cartridge (16). Chassis (30) further includes integral gripping features (40) that are exposed on opposite sides of housing assembly (24). Gripping features (40) have a surface geometry configured to promote an operator's grip of buttress applier cartridge (16) during use of buttress applier cartridge (16). Various suitable configurations that may be used for gripping features (40) will be apparent to those of ordinary skill in the art in view of the teachings herein. Similarly, various surface treatments (e.g., elastomeric material, etc.) that may be applied to gripping features (40) will be apparent to those of ordinary skill in the art in view of the teachings herein.

Actuator sleds (32) are slidably positioned on opposite faces of chassis (30). Arms (34) of actuator sleds (32) extend laterally inward to selectively and releasably secure buttress assemblies (12) to platform (30). In particular, FIG. 1 show arms (34) positioned such that buttress assemblies (12) are interposed between the free ends of arms (34) and platform (30). Arms (34) are movable laterally outwardly such that arms (34) disengage buttress assemblies (12) as shown in FIG. 2, thereby enabling buttress assemblies (12) to be removed from platform (30). In the present example, arms (34) are configured to bear against buttress assemblies (12), thereby pinching buttress assemblies (12) against platform (30). Other suitable ways in which arms (34) may engage buttress assemblies (12) will be apparent to those of ordinary skill in the art in view of the teachings herein.

B. Exemplary Buttress Assembly

Figure 3:
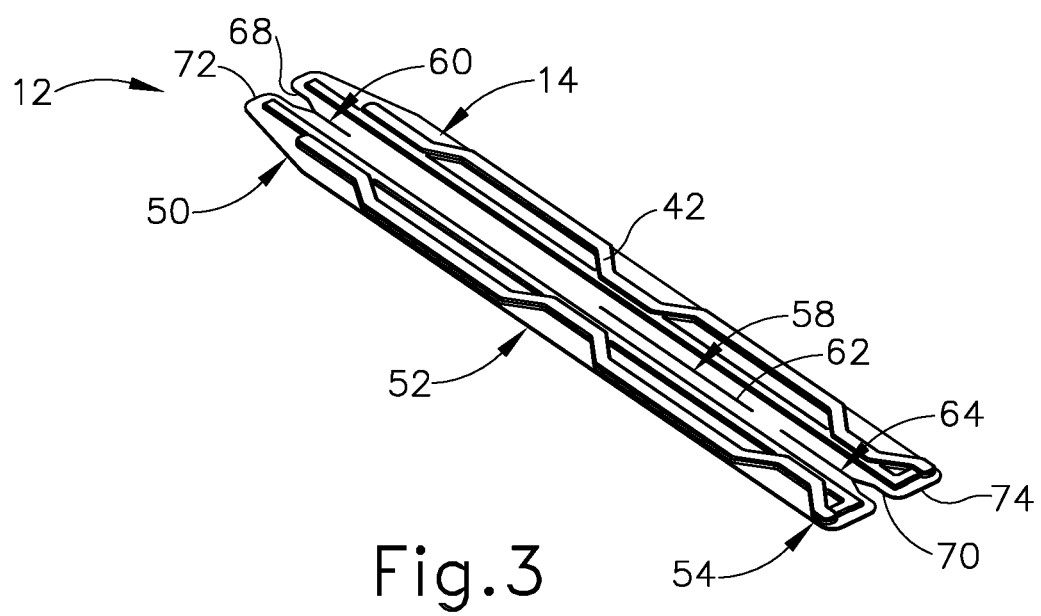
FIG. 3 depicts a perspective view of the buttress assembly of FIG. 1.
Figure 4:
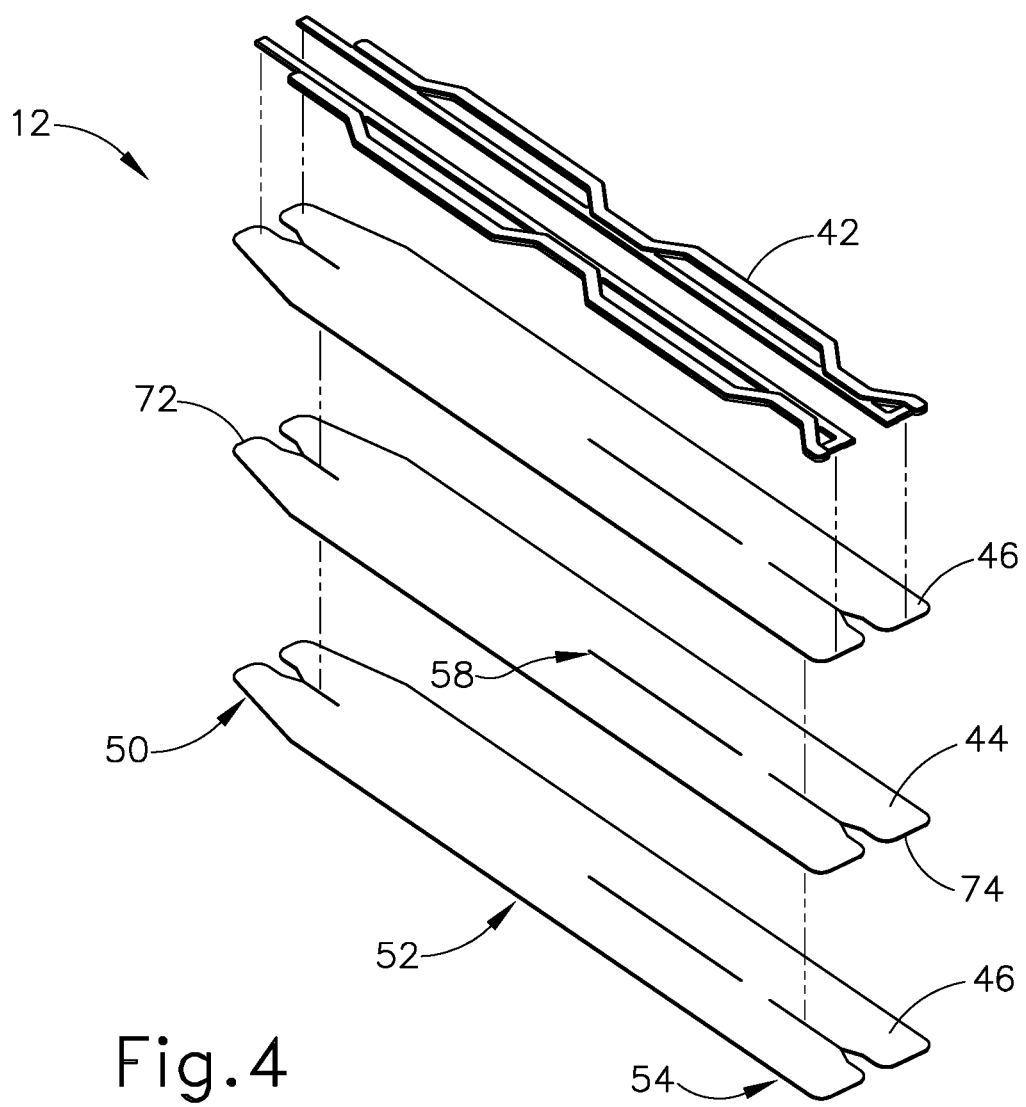
FIG. 4 depicts an exploded perspective view of the buttress assembly of FIG. 3.

FIG. 2 shows upper and lower buttress assemblies (12) removed from buttress applier cartridge (16), whereas FIG. 3 and FIG. 4 show upper buttress assembly (12) in more detail. Notably, in the present example, upper and lower buttress assemblies (12) are structurally identical, but for the relative positions of upper and lower buttress assemblies (12) retained on buttress applier cartridge (16). Buttress applier cartridge assembly (10) may thus be used in more than one orientation with surgical instrument (110) (see FIG. 10A). It will be appreciated that the following description of upper buttress assembly (12) similarly applies to lower buttress assembly (12) but for the respective orientations.

With respect to FIG. 3 and FIG. 4, upper buttress assembly (12) includes a buttress (14) and an upper adhesive layer (42). Buttress (14) of the present example more particularly has a three-layer, polymer construction including a core layer (44) sandwiched between two outer layers (46) to be collectively strong yet flexible to support a line of staples. In the present example, core layer (44) is a polyglactin 910 material, which is manufactured and sold by Ethicon, Inc. of Somerville, N.J. as VICRYL, whereas each outer layer is a polydioxanone (PDO) film material. More particularly, the polyglactin 910 material of core layer (44) in one example has a transverse thickness of 206 micrometers, while the polydioxanone (PDO) film material of each outer layer (46) has a transverse thickness of 8 micrometers. In another example, the polydioxanone (PDO) film material of each outer layer (46) has a transverse thickness of 9.5 micrometers. Buttress (14) of the present example is formed by laminating core layer (44) between outer layers (46) under a predetermined pressure, a predetermined temperature, and a predetermined time. Once laminated in one example, the polyglactin 910 material of core layer (44) has a transverse thickness of 161.5 micrometers. Such materials of layers (44, 46) in one example are composed of fibers arranged to extend in a direction 45 degrees from a longitudinally extending direction along each buttress assembly (12) to control lateral material stretch. Buttress (14) is further mechanically cut to size thereby inhibiting abrasive edges, such as burrs and/or delamination, that could damage sensitive tissues. It will be appreciated that alternative methods of cutting buttresses (14), such as a laser cutting or hot knife cutting, may be similarly used.

By way of further example only, each buttress (14) may comprise one or more portions of the following: NEOVEIL absorbable PGA felt by Gunze Limited, of Kyoto, Japan; SEAMGUARD polyglycolic acid: trimethylene carbonate (PGA:TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIO-DESIGN biologic graft material by Cook Medical, Bloomington, Ind.; and/or SURGICEL NU-KNIT hemostat material by Ethicon, Inc. of Somerville, N.J. Still other suitable materials that may be used to form each buttress (14) will be apparent to those of ordinary skill in the art in view of the teachings herein.

In addition or in the alternative, each buttress (14) may comprise a material including, for example, a hemostatic agent such as fibrin to assist in coagulating blood and reduce bleeding at the severed and/or stapled surgical site along tissue. As another merely illustrative example, each buttress (14) may comprise other adjuncts or hemostatic agents such as thrombin may be used such that each buttress (14) may assist to coagulate blood and reduce the amount of bleeding at the surgical site. Other adjuncts or reagents that may be incorporated into each buttress (14) may further include but are not limited to medical fluid or matrix components. Merely illustrative examples of materials that may be used to form each buttress (14), as well as materials that may be otherwise incorporated into each buttress (14), are disclosed in U.S. patent application Ser. No. 14/667,842, entitled "Method of Applying a Buttress to a Surgical Stapler," filed Mar. 25, 2015, the disclosure of which is incorporated by reference herein. Alternatively, any other suitable materials may be used.

By way of further example only, each buttress (14) may be constructed in accordance with at least some of the teachings of U.S. Patent Pub. No. 2012/0241493, entitled "Tissue Thickness Compensator Comprising Controlled Release and Expansion," published Sep. 27, 2012, the disclosure of which is incorporated by reference herein; U.S. Patent Pub. No. 2013/0068816, entitled "Surgical Instrument and Buttress Material," published Mar. 21, 2013, the disclosure of which is incorporated by reference herein; U.S. Pat. No. 9,999,408, entitled "Surgical Instrument with Fluid Fillable Buttress," issued Jun. 19, 2018, the disclosure of which is incorporated by reference herein; U.S. Pat. No. 8,814,025, entitled "Fibrin Pad Matrix with Suspended Heat Activated Beads of Adhesive," issued Aug. 26, 2014, the disclosure of which is incorporated by reference herein; U.S. Pat. No. 8,899,464, entitled "Attachment of Surgical Staple Buttress to Cartridge," issued Dec. 2, 2014, the disclosure of which is incorporated by reference herein; U.S. Pat. No. 9,492,170, entitled "Device for Applying Adjunct in Endoscopic Procedure," issued Nov. 15, 2016, the disclosure of which is incorporated by reference herein; U.S. Pat. No. 8,998,060, entitled "Resistive Heated Surgical Staple Cartridge with Phase Change Sealant," issued Apr. 7, 2015, the disclosure of which is incorporated by reference herein; U.S. Pat. No. 9,393,018, entitled "Surgical Staple Assembly with Hemostatic Feature," issued Jul. 19, 2016, the disclosure of which is incorporated by reference herein; U.S. Pat. No. 9,101,359, entitled "Surgical Staple Cartridge with Self-Dispensing Staple Buttress," issued Aug. 11, 2015, the disclosure of which is incorporated by reference herein; U.S. Pat. No. 9,198,644, entitled "Anvil Cartridge for Surgical Fastening Device," issued Dec. 1, 2015, the disclosure of which is incorporated by reference herein; U.S. Patent Pub. No. 2013/0075447, entitled "Adjunct Therapy for Applying Hemostatic Agent," published Mar. 28, 2013, the disclosure of which is incorporated by reference herein; U.S. Pat. No. 9,211,120, entitled "Tissue Thickness Compensator Comprising a Plurality of Medicaments," issued Dec. 15, 2015, the disclosure of which is incorporated by reference herein;

U.S. Patent Pub. No. 2015/0351758, entitled "Adjunct Materials and Methods of Using Same in Surgical Methods for Tissue Sealing," published Dec. 10, 2015, the disclosure of which is incorporated by reference herein; U.S. Patent Pub. No. 2017/0049444, entitled "Implantable Layers for a Surgical Instrument," published Feb. 23, 2017, the disclosure of which is incorporated by reference herein; U.S. Patent Pub. No. 2017/0055986, entitled "Drug Eluting Adjuncts and Methods of Using Drug Eluting Adjuncts," published Mar. 2, 2017, the disclosure of which is incorporated by reference herein; U.S. Patent Pub. No. 2017/0086837, entitled "Compressible Adjunct with Crossing Spacer Fibers," published Mar. 30, 2017, the disclosure of which is incorporated by reference herein; and/or U.S. Patent Pub. No. 2017/0086842, entitled "Method for Applying an Implantable Layer to a Fastener Cartridge," published Mar. 30, 2017, the disclosure of which is incorporated by reference herein.

Furthermore, buttress (14) is configured to be cut by a knife (114) (see FIG. 12A) from a proximal portion (50) of buttress (14), along an intermediate portion (52) of buttress (14), and further through a distal portion (54) of buttress (14) such that inward edges are adjacent to cut tissue as discussed below in more detail. Buttress (14) further includes a longitudinally extending pre-cut slit (58) configured to receive knife (114) (see FIG. 12A) and aid in separating lateral portions of buttress (14) as inward edges form therealong. Pre-cut slit (58) thus also reduces wear on knife (114) (see FIG. 12A) during use.

Pre-cut slit (58) of the present example has three distinct portions longitudinally separated by core and outer layers (44, 46). With respect to FIG. 5 and FIG. 6, a proximal portion of pre-cut slit (58) includes a proximal end slit (60) in proximal end portion (50) of buttress (14) extending entirely through buttress (14) in a transverse direction. An intermediate portion of pre-cut slit (58) includes an intermediate slit (62) in intermediate portion (52) of buttress (14) extending entirely through buttress (14) in the transverse direction. Furthermore, a distal portion of pre-cut slit (58) includes a distal end slit (64) extending entirely through buttress (14) in the transverse direction. In the present example, proximal end slit (60), intermediate slit (62), and distal end slit (64) are longitudinally aligned along a central longitudinal axis that laterally bifurcates lateral halves of buttress (14). Intermediate slit (62) is spaced apart from each of proximal and distal end slits (60, 64) such that the portions of buttress (14) between slits (60, 62, 64) remain uncut. Such uncut portions that may also be referred to as "bridge" portions are sized large enough to remain intact during assembly, storage, and application with tissue, but small enough to substantially reduce resistance while cutting buttress (14). However, it will be appreciated that some further perforation may be formed along the central longitudinal axis in alternative examples to further aid severability between lateral halves of buttress (14).

Proximal end slit (60) and distal end slit (64) portions of pre-cut slit (58) further include a proximal end opening (68) and a distal end opening (70), respectively. Proximal end opening (68) of proximal end slit (60) widens symmetrically about the central longitudinal axis to a proximal end (72) of buttress (14), whereas distal end opening (70) of distal end slit (64) widens symmetrically about the central longitudinal axis to a distal end (74) of buttress (14). Such widened proximal and distal end openings (68, 70) are configured to respectively aid knife's (114) introduction and departure from buttress (14) while cutting as discussed below in greater detail.

Figure 7:
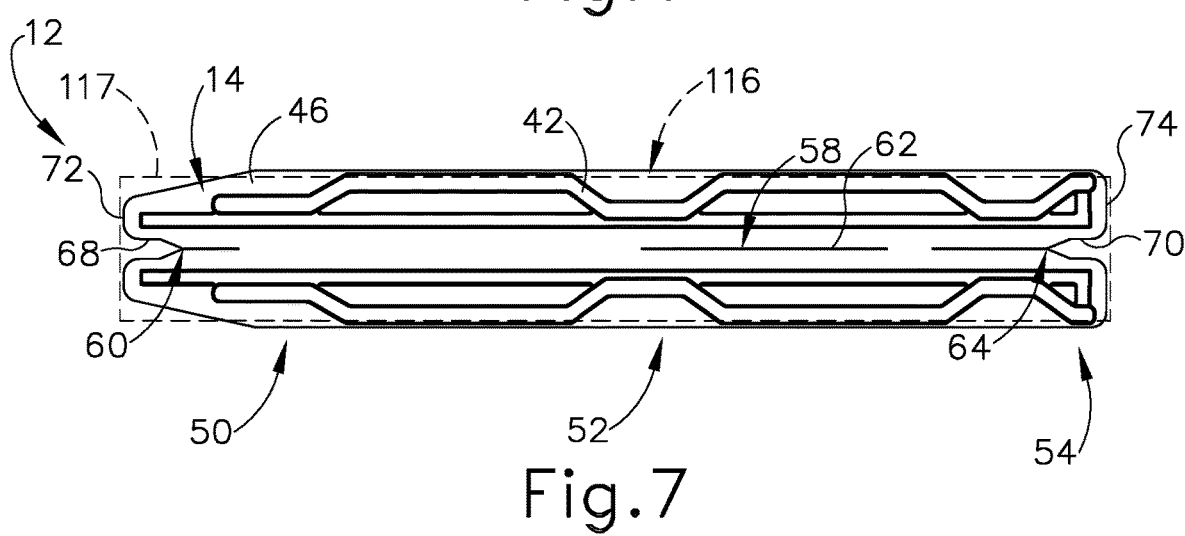
FIG. 7 depicts a top view of the buttress assembly of FIG. 1 for the upper jaw showing an outer profile of the upper jaw thereon.

With respect to FIG. 7, upper adhesive layer (42) is provided on outer layer (46) of buttress (14) in order to adhere buttress (14) within effector (112) (see FIG. 10A) of surgical instrument (110) (see FIG. 10A). Adherence of the buttress (14) can occur through a variety of mechanisms including but not limited to a pressure sensitive adhesive. In some versions, each adhesive layer (42) includes a pressure sensitive adhesive material. Examples of various suitable materials that may be used to form adhesive layers (42) are disclosed in U.S. Patent Pub. No. 2016/0278774, entitled "Method of Applying a Buttress to a Surgical Stapler," published Sep. 29, 2016, the disclosure of which is incorporated by reference herein. Alternatively, any other suitable materials may be used. As shown in the present example, adhesive layer (42) is applied to form a continuous outer seal to enhance longevity once applied to end effector (112) (see FIG. 10A).

It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (42) will be apparent to those of ordinary skill in the art in view of the teachings herein.

Figure 5:
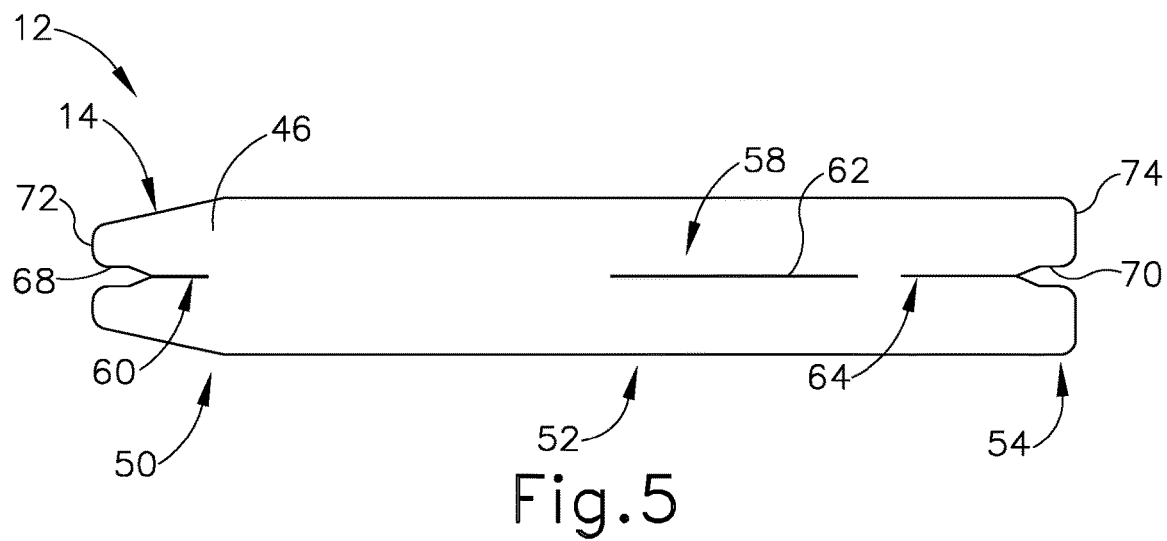
FIG. 5 depicts a bottom view of the buttress assembly of FIG. 1 for the upper jaw.
Figure 6:
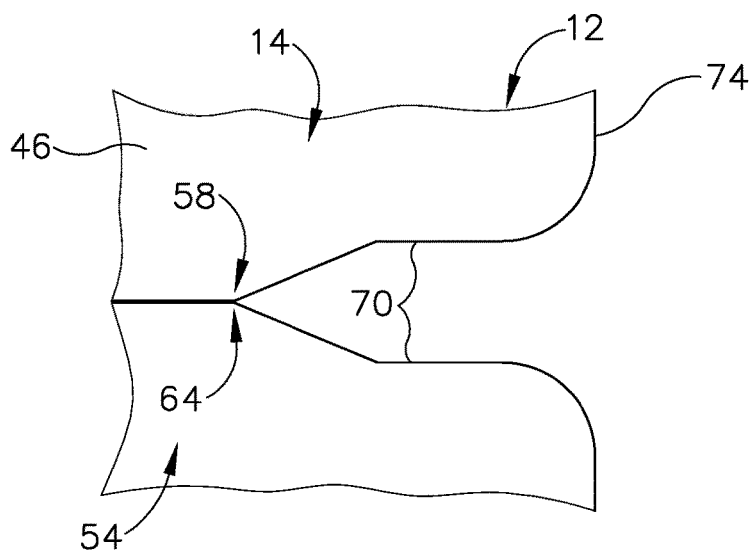
FIG. 6 depicts an enlarged bottom view of a distal end portion of the buttress assembly of FIG. 1 showing a pre-formed slit.
Figure 8:
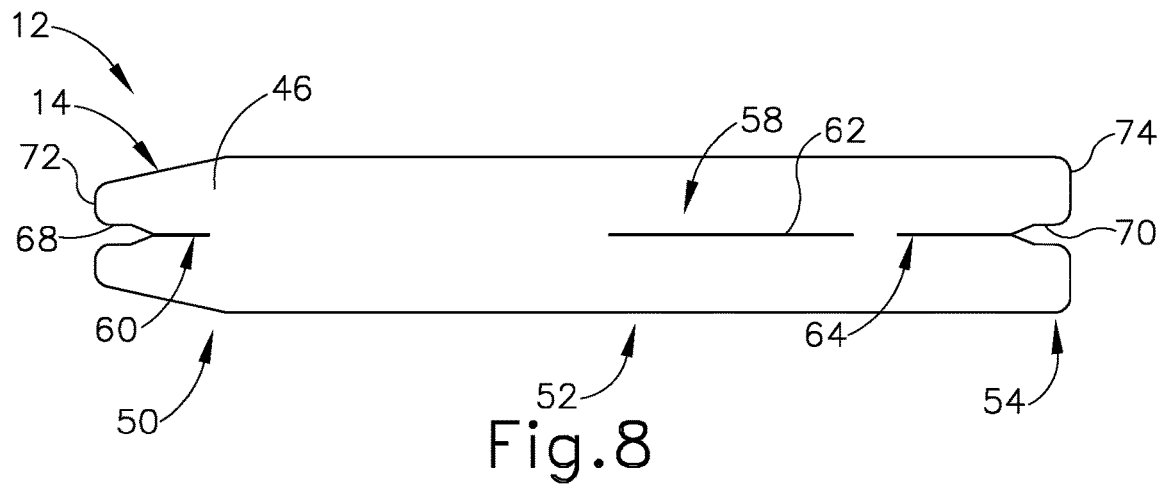
FIG. 8 depicts a top view of the buttress assembly of FIG. 1 for the lower jaw.
Figure 9:
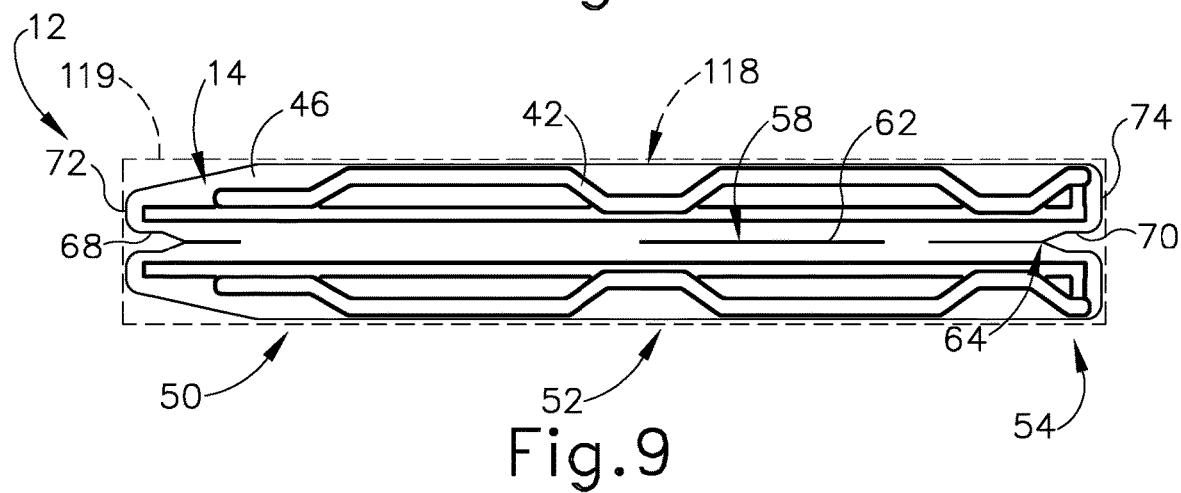
FIG. 9 depicts a bottom view of the buttress assembly of FIG. 1 for the lower jaw showing an outer profile of the lower jaw thereon.

As generally discussed above and with respect to FIGS. 5-9, upper and lower buttress assemblies (12) are structurally identical. In this respect, FIG. 5 shows a lower surface of upper buttress assembly (12) from a lower transverse direction, whereas FIG. 8 shows an upper surface of lower buttress assembly (12) from an upper transverse direction. These lower and upper surfaces of the present example have the same lateral width and longitudinal lengths. Similarly, FIG. 7 shows an upper surface of upper buttress assembly (12) from an upper transverse direction, whereas FIG. 9 shows an lower surface of lower buttress assembly (12) from a lower transverse direction. In each instance in the present example, these lower and upper surfaces have the same lateral width and longitudinal lengths. In addition, adhesive layers (42) of each respective buttress assembly (12) are formed as adhesive bead layers (42) in a predetermined adhesive pattern. The adhesive pattern for each of the upper and lower buttress assemblies (12) shown respectively in FIG. 7 and FIG. 9 is again identical, having the same lateral width and longitudinal lengths. The lateral width and longitudinal length of the adhesive pattern collectively define an outer adhesive profile sized to accommodate both an anvil (116) and a deck (118) of a staple cartridge (120). In other words, the outer adhesive profile of adhesive layer (42) as well as buttress (14) are interchangeable with anvil (116) and deck (118) such that buttress applier cartridge assembly (10) may be used in an upright orientation or flipped about the central longitudinal axis in an upside-down orientation while loading end buttress assemblies (12) for use.

To this end, FIG. 7 shows an outer anvil profile (117) overlaid onto upper buttress assembly (12), and FIG. 9 shows an outer deck profile (119) overlaid onto lower buttress assembly (12) to illustrate the interface between the adhesive pattern of adhesive layer (42) with an underside (122) of anvil (116) and deck (118). The adhesive pattern of the present example is symmetric about the central longitudinal axis such that upper adhesive layer (42) mirrors lower adhesive layer (42) in lateral and longitudinal alignment when arranged offset from each other on platform (30) (see FIG. 1). More particularly, each adhesive layer (42) of the present example has a lateral width generally equivalent to the lateral width of outer deck profile (119), but larger than the lateral width of outer anvil profile (117). Adhesive layer (42) thereby fits within outer deck profile (119) of FIG. 9 with a greater surface area contact to deck (118) to increase adhesive force therebetween. However, adhesive layer (42) is laterally wider than outer anvil profile (117) of FIG. 7 and extends laterally beyond outer anvil profile (117) with less surface area contact to underside (122) of anvil to decrease adhesive force therebetween. More particularly, each adhesive layer (42) of the present example has a lateral width of approximately 0.41 inches. In contrast, deck (118) is wider than underside (122) of anvil (116) with deck (118) having a lateral width of approximately 0.41 inches, and underside (122) of anvil (116) having a lateral width of approximately 0.37 inches.

While the above referenced interchangeability between anvil (116) and deck (118) simplifies loading buttress assemblies (12) and reduces the likelihood of improper loading, the reduced surface area contact between underside (122) of anvil (116) and adhesive layer (42) eases removal of buttress assembly (12) from anvil (116). In one example, underside (122) of anvil (116) is a relatively smooth material that adheres to buttress (14) via adhesive layer (42) with a relatively higher adhesive force than the relatively lower adhesive force of buttress assembly (12) to deck (118). Decreasing the surface area contact between adhesive layer (42) and underside (122) of anvil (116) relative to the surface area contact with deck (118) may thus result in more equalized and/or predictable removal forces of buttress assemblies (12) from anvil (116) and deck (118).

C. Exemplary Adhesion of Buttress to Surgical Stapler and Cutting of Buttress Assembly with Tissue As noted above and discussed below in greater detail with respect to FIG. 10A, upper and lower buttress assemblies (12) include upper and lower adhesive layers (42) (or other form of adhesive material) to adhere respective buttresses (14) to an underside (122) of anvil (116) and deck (118) of staple cartridge (120). Such adhesive may provide proper positioning of buttress (14) before and during actuation of end effector (112); then allow buttress (14) to separate from end effector (112) after end effector (112) has been actuated, without causing damage to buttress (14) that is substantial enough to compromise the proper subsequent functioning of buttress (14).

Figure 10B:
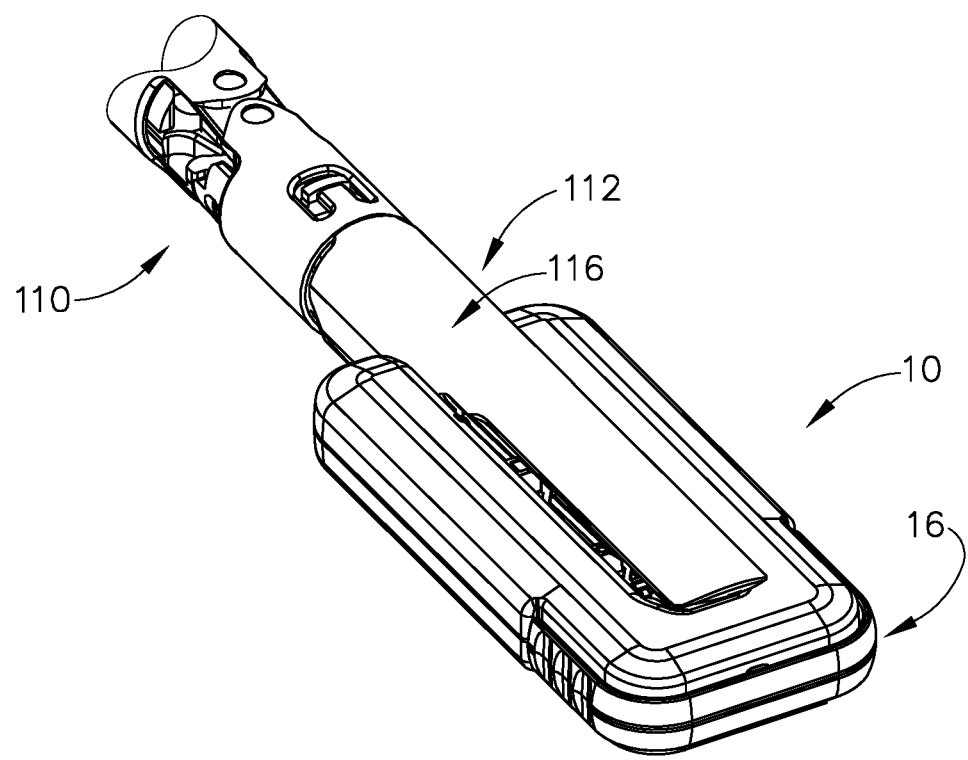
FIG. 10B depicts the perspective view of the end effector similar to FIG. 10B, but showing the buttress applier cartridge assembly of FIG. 1 positioned between the upper and lower jaws in a closed position.
Figure 10C:
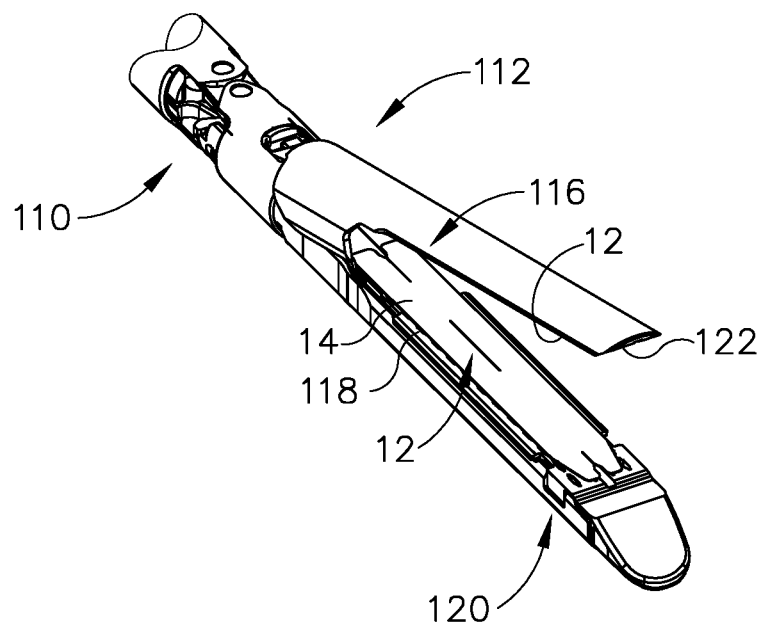
FIG. 10C depicts the perspective view of the end effector similar to FIG. 10B, but showing the buttress assemblies respectively secured to the upper and lower jaws in the open position.

To use buttress applier cartridge (16) to load end effector (112), the operator would first position buttress applier cartridge (16) and end effector (112) such that end effector (112) is aligned with open end (18) of buttress applier cartridge (16) as shown in FIG. 10A. The operator would then advance end effector (40) distally (and/or retract buttress applier cartridge (16) proximally) to position platform (30) and buttress assemblies (12) between anvil (116) and staple cartridge (120). In order to load buttress assemblies (12) on end effector (112), the operator simply closes end effector (112) by pivoting anvil (116) toward staple cartridge (120) to reach the state shown in FIG. 10B. As shown, closure of end effector (40) results in anvil (60) and staple cartridge (120) bearing against actuator sleds (32), thereby urging arms (34) to unlock buttress assemblies (12) from buttress applier cartridge (16). Adhesive layers (42) of upper and lower buttress assemblies (12) are sufficiently compressed against anvil (116) and deck (118) as shown in FIG. 10C to retain upper and lower buttress assemblies (12) to end effector (112) for stapling tissue.

To this end, FIGS. 11A-11C show a sequence where end effector (112) loaded with buttress assemblies (12) is actuated to drive a plurality of staples (124) through two apposed layers of tissue ($T_1$, $T_2$), with buttress assemblies (12) being secured to the same layers of tissue ($T_1$, $T_2$) by staples (124). In particular, FIG. 11A shows layers of tissue ($T_1$, $T_2$) positioned between anvil (116) and staple cartridge (120), with anvil (116) in the open position. Upper buttress assembly (12) is adhered to the underside (122) of anvil (116) via adhesive layer (42); while lower buttress assembly (12) is adhered to deck (118) of staple cartridge (120) via adhesive layer (42). Layers of tissue ($T_1$, $T_2$) are thus interposed between upper and lower buttress assemblies (12). Next, a trigger (not shown) is pivoted to drive anvil (116) to the closed position as shown in FIG. 11B. At this stage, layers of tissue ($T_1$, $T_2$) are compressed between anvil (116) and staple cartridge (120), with upper and lower buttress assemblies (12) engaging opposite surfaces of tissue layers ($T_1$, $T_2$). End effector (112) is then actuated as described above, driving staple (124) through upper and lower buttress assemblies (12) and layers of tissue ($T_1$, $T_2$). As shown in FIG. 11C, a crown (126) of driven staple (124) captures and retains lower buttress assembly (12) against layer of tissue ($T_2$). Deformed legs (128) of staple (124) capture and retain upper buttress assembly (12) against layer of tissue ($T_1$).

It should be understood that a series of staples (124) will similarly capture and retain upper and lower buttress assemblies (12) against layers of tissue ($T_1$, $T_2$), thereby securing upper and lower buttress assemblies (12) to tissue ($T_1$, $T_2$). As can also be seen in FIGS. 12A-12D, knife (114) also cuts through a centerline of buttress assemblies (12), separating each buttress assembly (12) into a corresponding pair of sections, such that each section remains secured to a respective severed region of tissue ($T_1$, $T_2$). For example, with tissue ($T_1$, $T_2$) stapled as shown in FIG. 11C, knife (114) is driven distally from a proximal position severing tissue ($T_1$, $T_2$) and upper and lower buttress assemblies (12).

Figure 12A:
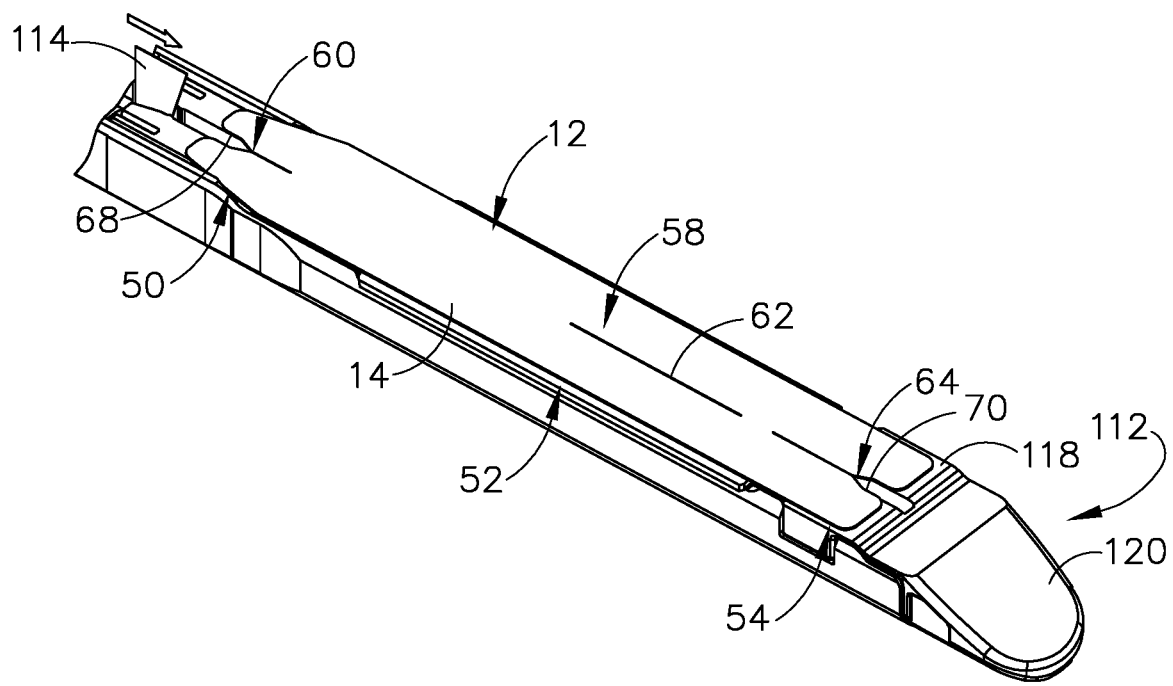
FIG. 12A depicts a perspective view of the buttress assembly of FIG. 10C secured to the lower jaw of FIG. 10C and a knife of the end effector being driven distally therethrough.
Figure 12B:
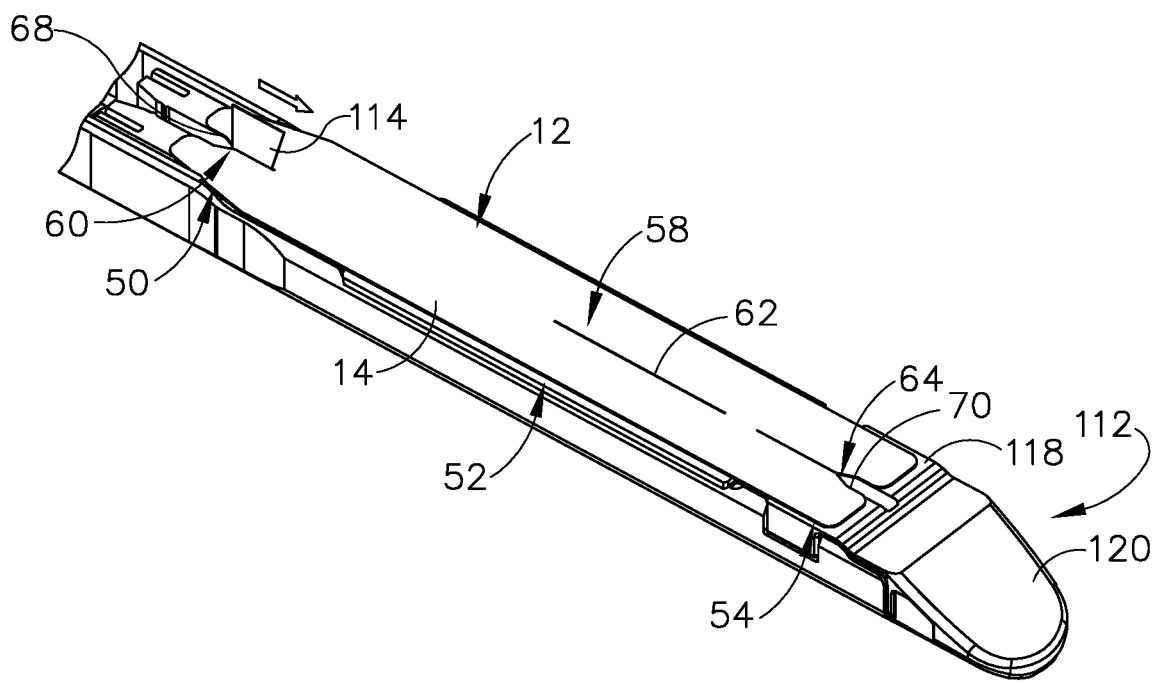
FIG. 12B depicts the perspective view of the buttress assembly and the lower jaw similar to FIG. 12A, but showing the knife cutting a proximal portion of the buttress assembly while being driven distally therethrough.

FIGS. 12A-12D illustrate knife severing buttress assemblies (12) and tissue ($T_1$, $T_2$) as shown in FIG. 11C, but with tissue ($T_1$, $T_2$), upper buttress assembly (12), and anvil (116) hidden for additional clarity. As shown in FIGS. 12A-12B, knife (114) is introduced into proximal end opening (68) and further through the remainder of proximal end slit (60). Proximal end slit (60) thereby inhibits buttress (14) from gathering onto knife (114) with staggered, uneven cutting in the event that tissue ($T_1$, $T_2$) is not compressed against proximal portion (50) of buttress (14).

Figure 12C:
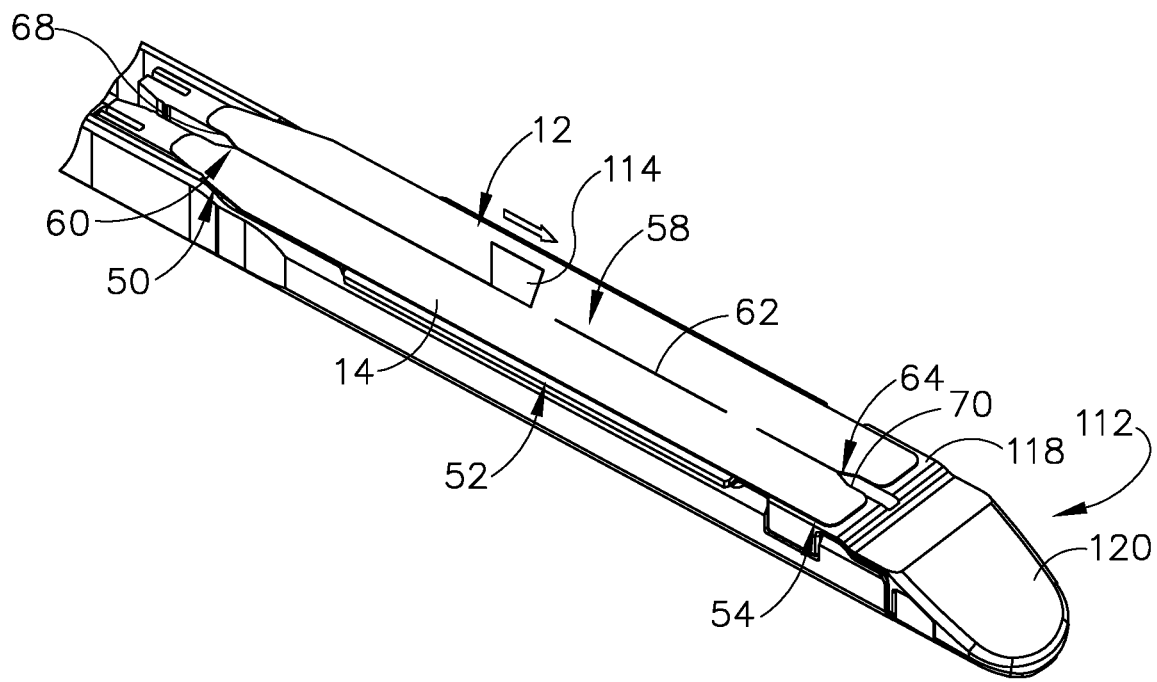
FIG. 12C depicts the perspective view of the buttress assembly and the lower jaw similar to FIG. 12B, but showing the knife cutting an intermediate portion of the buttress assembly while being driven distally therethrough.
Figure 12D:
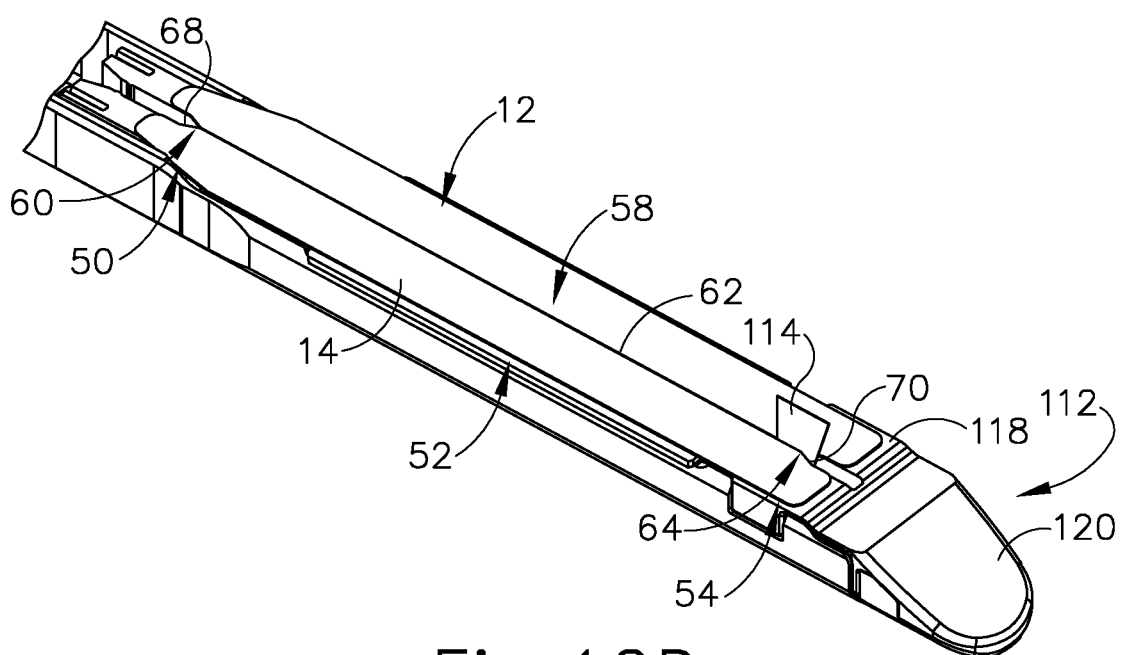
FIG. 12D depicts the perspective view of the buttress assembly and the lower jaw similar to FIG. 12C, but showing the knife cutting a distal portion of the buttress assembly while being driven distally therethrough.

With respect to FIG. 12C, knife (114) distally translates from proximal end slit (60) of pre-cut slit (58) severing proximal and intermediate portions (50, 52) of buttress (14) until received within intermediate slit (62) of pre-cut slit (58). Intermediate slit (62) reduces the likelihood of inadvertently tearing intermediate and/or distal portions (52, 54) of buttress (14) in the event that tissue ($T_1$, $T_2$) is only compressed against the proximal portion (50) and not present against the intermediate and distal portions (52, 54) of buttress (14). As knife (114) cuts from intermediate portion (52) of buttress (14) through distal portion (54) of buttress (14), FIG. 12D shown knife (114) departing through distal end opening (70) to the distal position having severed buttress assembly (12) into a pair of lateral halves. Distal end slit (64) is sized to accommodate manufacturing tolerances associated with the particular position of knife's (114) distal position to ensure that buttress assembly (12) is fully severed into two lateral halves upon completion without requiring the operator to manually rip or cut a remaining distal portion of buttress (14).

Figure 13:
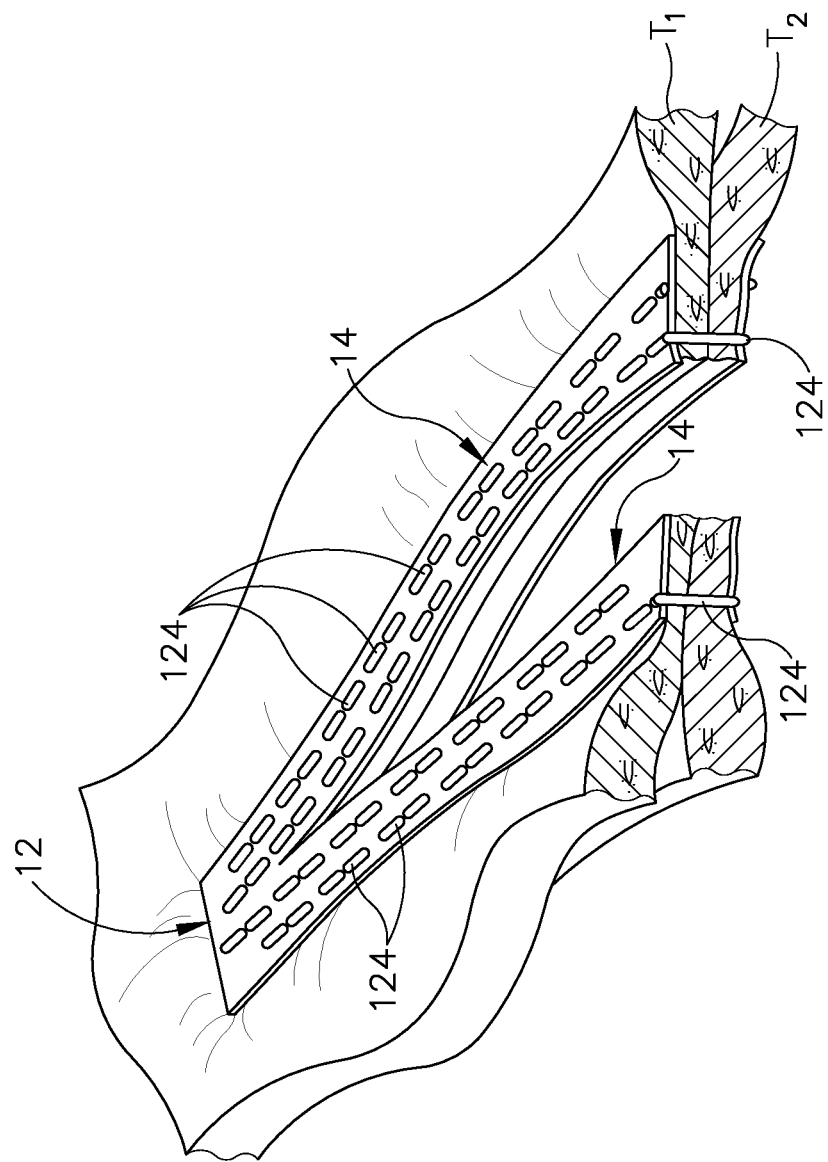
FIG. 13 depicts a perspective view of staples and the buttress assembly of FIG. 12D having been secured to the tissue by the end effector as shown in FIG. 11C and cut as shown in FIG. 12D.

With respect to FIG. 13, as end effector (112) (see FIG. 12D) is pulled away from tissue ($T_1$, $T_2$) after deploying staples (124) and upper and lower buttress assemblies (12), upper and lower buttress assemblies (12) disengage end effector (112), such that upper and lower buttress assemblies (12) remain secured to tissue ($T_1$, $T_2$) with staples (124). Buttressed tissue ($T_1$, $T_2$) thus provides structural reinforcement to the lines of staples (124). In addition to the foregoing, it should also be understood that any of the various buttress assemblies described herein may be further constructed and operable in accordance with at least some of the teachings of U.S. Patent Pub. No. 2016/0278774, entitled "Method of Applying a Buttress to a Surgical Stapler," published Sep. 29, 2016, the disclosure of which is incorporated by reference herein.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical system for stapling tissue, comprising: (a) a buttress applier cartridge, including: (i) a housing defining a first gap and a second gap extending in a longitudinal direction therealong such that each of the first and second gaps are configured to receive a first portion of an end effector and a second portion of the end effector of a surgical stapler, and (ii) a platform connected to the housing and exposed in a transverse direction between the first and second gaps and supported by the housing, (b) a first buttress assembly positioned on the platform and exposed in the first gap of the housing, wherein the first buttress includes: (i) a first buttress configured to be received against tissue and support a staple formed therein, and (ii) a first adhesive layer on the first buttress exposed in the first gap of the housing and configured to releasably adhere the first buttress against the first or second portion of the end effector, wherein the first adhesive layer is parallel to the first buttress and defines a first adhesive pattern having a first outer adhesive profile; and (c) a second buttress assembly positioned on the platform and exposed in the second gap of the housing, wherein the second buttress includes: (i) a second buttress configured to be received against tissue and support the staple formed therein, and (ii) a second adhesive layer on the second buttress exposed in the second gap of the housing and configured to releasably adhere the second buttress against the first or second portion of the end effector, wherein the second adhesive layer is parallel to the second buttress and defines a second adhesive pattern having a second outer adhesive profile, wherein the exposed second outer adhesive profile in the transverse direction is the same as the exposed first outer adhesive profile in an opposite transverse direction such that the first and second buttress assemblies are interchangeable with the first and second portions of the end effector of the surgical instrument.

Example 2

The surgical system of Example 1, wherein the second adhesive pattern of the second adhesive layer mirrors the first adhesive pattern of the first adhesive layer through the platform.

Example 3

The surgical system of any one or more of Examples 1 through 2, wherein the first buttress assembly is transversely offset from and transversely aligned with the second buttress assembly.

Example 4

The surgical system of any one or more of Examples 1 through 3, wherein the first outer adhesive profile is transversely offset from and transversely aligned with the second outer adhesive profile.

Example 5

The surgical system of any one or more of Examples 1 through 4, wherein the first adhesive layer is a first adhesive bead layer, and wherein the second adhesive layer is a second adhesive bead layer.

Example 6

The surgical system of any one or more of Examples 1 through 5, wherein the first buttress assembly has a first lateral buttress width in a lateral direction perpendicular to the longitudinal and transverse directions, wherein the second buttress assembly has a second lateral buttress width in the lateral direction perpendicular to the longitudinal and transverse directions, wherein the first and second lateral buttress widths are each the same.

Example 7

The surgical system of Example 6, wherein the first and second lateral buttress widths are each 0.41 inches.

Example 8

The surgical system of any one or more of Examples 1 through 7, wherein the first and second adhesive layers are each configured to adhere to an anvil of the end effector and a staple cartridge of an end effector, wherein the first and second adhesive layers are each configured to adhere to the anvil with a lesser adhesive surface area for relatively reduced adhesion thereto, and wherein the first and second adhesive layers are configured to adhere to the staple cartridge with a greater adhesive surface area for relatively increased adhesion thereto.

Example 9

The surgical system of Example 8, wherein the first and second outer adhesive profiles are each configured to laterally fit within an outer stapler cartridge profile of the staple cartridge adhered thereto in a lateral direction perpendicular to the longitudinal and transverse directions, and wherein the first and second outer adhesive profiles are each configured to laterally extend beyond an outer anvil profile of the anvil adhered thereto in the lateral direction perpendicular to the longitudinal and transverse directions.

Example 10

The surgical system of Example 9, further comprising a surgical stapler having an end effector, wherein the end effector includes a staple cartridge movably mounted relative to an anvil and the staple cartridge removably adhered to one of the first or second buttress assemblies and the anvil removably adhered to the other of the first or second buttress assemblies, wherein one of the first or second outer adhesive profiles laterally fits within the outer stapler cartridge profile of the staple cartridge adhered thereto, and wherein the other of the first or second outer adhesive profiles laterally extends beyond the outer anvil profile of the anvil adhered thereto.

Example 11

The surgical system of any one or more of Examples 1 through 10, wherein at least one of the first or second buttresses has a pre-cut slit extending longitudinally therealong, wherein the pre-cut slit is configured to receive a knife for separating the at least one of the first or second buttress assemblies.

Example 12

The surgical system of Example 11, wherein the at least one of the first or second buttresses includes a distal buttress end portion, a proximal buttress end portion, and an intermediate buttress portion extending therebetween, wherein the pre-cut slit includes at least one of a proximal end slit longitudinally extending through the proximal buttress end portion to a proximal end of the proximal buttress end portion, a distal end slit longitudinally extending through the distal buttress end portion to a distal end of the distal buttress end portion, or an intermediate slit longitudinally extending through the intermediate buttress portion.

Example 13

The surgical system of Example 12, wherein the pre-cut slit includes each of the proximal end slit, the distal end slit, and the intermediate slit therebetween, and wherein the intermediate slit is longitudinally spaced apart from each of the proximal and distal end slits.

Example 14

The surgical system of any one or more of Examples 1 through 13, wherein at least one of the first or second buttresses has a core layer sandwiched between a pair of outer layers.

Example 15

The surgical system of Example 14, wherein the core layer is a polyglactin 910 material, and wherein the outer layers are each a polydioxanone film material.

Example 16

A buttress applier cartridge assembly, comprising: (a) a buttress assembly configured to be positioned on a platform and exposed in a gap of a housing, wherein the buttress assembly includes: (i) a buttress extending longitudinally from a proximal buttress end portion to a distal buttress end portion with an intermediate buttress portion extending therebetween, wherein the buttress is configured to be received against tissue and support a staple formed therein, (ii) an adhesive layer on the buttress extending in a longitudinal direction and a lateral direction perpendicular to the longitudinal direction, wherein the adhesive layer is configured to be exposed in the gap of the housing and further configured to releasably adhere the buttress against an end effector of a surgical stapler, and (iii) a pre-cut slit extending longitudinally through the buttress and configured to receive a knife as the knife cuts through a proximal buttress end portion through the intermediate buttress portion to the distal buttress end portion, wherein the pre-cut slit is configured to encourage separating a first lateral portion of the buttress from a second lateral portion of the buttress.

Example 17

The buttress applier cartridge of Example 16, wherein the pre-cut slit includes a proximal end slit longitudinally extending through the proximal buttress end portion to a proximal end of the proximal buttress end portion.

Example 18

The buttress applier cartridge of any one or more of Examples 16 through 17, wherein the pre-cut slit includes a distal end slit longitudinally extending through the distal end portion to a distal end of the distal buttress end portion.

Example 19

The buttress applier cartridge of Examples 16 through 18, wherein the pre-cut slit includes an intermediate slit longitudinally extending through the intermediate buttress portion.

Example 20

A buttress applier cartridge assembly, comprising: (a) a buttress assembly configured to be positioned on a platform and exposed in a gap of a housing, wherein the buttress assembly includes: (i) a buttress configured to be received against tissue and support a staple formed therein, wherein the buttress includes: (A) a first outer film layer, (B) a second outer film layer, and (C) a core mesh layer laminated between the first and second outer layers; and (ii) an adhesive layer on the first outer layer configured to be exposed in the gap of the housing and further configured to releasably adhere the buttress against an end effector of a surgical stapler, wherein each of the first and second outer film layers, the core mesh layer, and the adhesive layer are configured to be absorbed by tissue.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. Patent Pub. No. 2016/0278774, entitled "Method of Applying a Buttress to a Surgical Stapler," published Sep. 29, 2016, the disclosure of which is incorporated by reference herein; U.S. Patent Pub. No. 2017/0049444, entitled "Implantable Layers for a Surgical Instrument," published Feb. 23, 2017, the disclosure of which is incorporated by reference herein; U.S. Patent Pub. No. 2017/0086837, entitled "Compressible Adjunct with Crossing Spacer Fibers," published Mar. 30, 2017, the disclosure of which is incorporated by reference herein; and U.S. Patent Pub. No. 2017/0086842, entitled "Method for Applying an Implantable Layer to a Fastener Cartridge," published Mar. 30, 2017, the disclosure of which is incorporated by reference herein. Furthermore, in addition to the methods described herein, any of the various buttress assemblies described herein may be applied to end effector (40) in accordance with at least some of the teachings of U.S. Provisional Patent App. No. 62/209,041, entitled "Method and Apparatus for Applying a Buttress to End Effector of a Surgical Stapler," filed Aug. 24, 2015, the disclosure of which is incorporated by reference herein; and/or U.S. Patent Pub. No. 2017/0086842, entitled "Method for Applying an Implantable Layer to a Fastener Cartridge," published Mar. 30, 2017, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical system for stapling tissue, comprising:
  (a) a buttress applier cartridge, including:
    (i) a housing defining a first gap and a second gap extending in a longitudinal direction therealong such that the first and second gaps are configured to receive a first portion of an end effector and a second portion of the end effector, respectively, of a surgical stapler, and
    (ii) a platform connected to the housing and exposed in a transverse direction between the first and second gaps and supported by the housing;
  (b) a first buttress assembly positioned on the platform and exposed in the first gap of the housing, wherein the first buttress assembly includes:
    (i) a first buttress configured to be received against tissue and support a staple formed therein, and
    (ii) a first adhesive layer on a side of the first buttress and configured to releasably adhere the first buttress against the first or second portion of the end effector, wherein the first adhesive layer is parallel to the first buttress and comprises a first adhesive bead layer that defines a first adhesive pattern having a first outer adhesive profile, wherein the first adhesive bead layer includes a plurality of first elongate bead portions that extend parallel to a longitudinal centerline of the first buttress assembly, wherein the first adhesive bead layer encloses a plurality of regions of the side of the first buttress that are free of adhesive; and

(c) a second buttress assembly positioned on the platform and exposed in the second gap of the housing, wherein the second buttress assembly includes:
  (i) a second buttress configured to be received against tissue and support the staple formed therein, and
  (ii) a second adhesive layer on a side of the second buttress and configured to releasably adhere the second buttress against the first or second portion of the end effector, wherein the second adhesive layer is parallel to the second buttress and comprises a second adhesive bead layer that defines a second adhesive pattern having a second outer adhesive profile, wherein the second adhesive bead layer includes a plurality of second elongate bead portions that extend parallel to a longitudinal centerline of the second buttress assembly, wherein the second adhesive bead layer encloses a plurality of regions of the side of the second buttress that are free of adhesive,
wherein the second outer adhesive profile in the transverse direction is the same as the first outer adhesive profile in an opposite transverse direction such that the first and second buttress assemblies are interchangeable with the first and second portions of the end effector of the surgical instrument.

2. The surgical system of claim 1, wherein the second adhesive pattern of the second adhesive layer mirrors the first adhesive pattern of the first adhesive layer through the platform.

3. The surgical system of claim 1, wherein the first buttress assembly is transversely offset from and transversely aligned with the second buttress assembly.

4. The surgical system of claim 1, wherein the first outer adhesive profile is transversely offset from and transversely aligned with the second outer adhesive profile.

5. The surgical system of claim 1, wherein the first buttress assembly has a first lateral buttress width in a lateral direction perpendicular to the longitudinal and transverse directions, wherein the second buttress assembly has a second lateral buttress width in the lateral direction perpendicular to the longitudinal and transverse directions, wherein the first and second lateral buttress widths are each the same.

6. The surgical system of claim 5, wherein the first and second lateral buttress widths are each 0.41 inches.

7. The surgical system of claim 1, wherein the first and second adhesive layers are each configured to adhere to an anvil of the end effector and a deck of the end effector, wherein the first and second adhesive layers are each configured to adhere to the anvil with a lesser adhesive surface area for relatively reduced adhesion thereto, and wherein the first and second adhesive layers are configured to adhere to the deck with a greater adhesive surface area for relatively increased adhesion thereto.

8. The surgical system of claim 7, wherein the first and second outer adhesive profiles are each configured to laterally fit within an outer deck profile of the deck adhered thereto in a lateral direction perpendicular to the longitudinal and transverse directions, and wherein the first and second outer adhesive profiles are each configured to laterally extend beyond an outer anvil profile of the anvil adhered thereto in the lateral direction perpendicular to the longitudinal and transverse directions.

9. The surgical system of claim 8, further comprising a surgical stapler having an end effector that includes a deck that defines the outer deck profile and an anvil that defines the outer anvil profile, wherein the deck is removably adhered to one of the first or second buttress assemblies and the anvil is removably adhered to the other of the first or second buttress assemblies, wherein one of the first or second outer adhesive profiles laterally fits within the outer deck profile of the deck adhered thereto, and wherein the other of the first or second outer adhesive profiles laterally extends beyond the outer anvil profile of the anvil adhered thereto.

10. The surgical system of claim 1, wherein at least one of the first or second buttresses has a pre-cut slit extending longitudinally therealong, wherein the pre-cut slit is configured to receive a knife for separating the at least one of the first or second buttress assemblies.

11. The surgical system of claim 10, wherein the at least one of the first or second buttresses includes a distal buttress end portion, a proximal buttress end portion, and an intermediate buttress portion extending therebetween, wherein the pre-cut slit includes at least one of a proximal end slit longitudinally extending through the proximal buttress end portion in a proximal direction to a proximal end of the proximal buttress end portion, a distal end slit longitudinally extending through the distal buttress end portion in a distal direction to a distal end of the distal buttress end portion, or an intermediate slit longitudinally extending through the intermediate buttress portion.

12. The surgical system of claim 11, wherein the pre-cut slit includes each of the proximal end slit, the distal end slit, and the intermediate slit therebetween, and wherein the intermediate slit is longitudinally spaced apart from each of the proximal and distal end slits.

13. The surgical system of claim 1, wherein at least one of the first or second buttresses has a core layer sandwiched between a pair of outer layers.

14. The surgical system of claim 13, wherein the core layer is a polyglactin 910 material, and wherein the outer layers are each a polydioxanone film material.

15. The surgical system of claim 1, wherein each of the first elongate bead portions is laterally spaced apart from a respective side of the longitudinal centerline of the first buttress assembly, wherein each of the second elongate bead portions is laterally spaced apart from a respective side of the longitudinal centerline of the second buttress assembly.

16. The surgical system of claim 1, wherein a maximum lateral width of the first adhesive pattern is less than a maximum lateral width of the first buttress, wherein a maximum lateral width of the second adhesive pattern is less than a maximum lateral width of the second buttress.

17. A buttress applier cartridge assembly, comprising:
(a) a buttress assembly configured to be positioned on a platform and exposed in a gap of a housing, wherein the buttress assembly includes:
  (i) a buttress extending longitudinally from a proximal buttress end portion to a distal buttress end portion with an intermediate buttress portion extending therebetween, wherein the buttress is configured to be received against tissue and support a staple formed therein,
  (ii) an adhesive layer on the buttress, wherein the adhesive layer is configured to be exposed in the gap of the housing and further configured to releasably adhere the buttress against an end effector of a surgical stapler, and (iii) a pre-cut slit feature extending along a longitudinal centerline of the buttress assembly and configured to promote cutting of the buttress by a knife into first and second lateral buttress portions, wherein the pre-cut slit feature consists of:
 (A) a first end slit extending longitudinally through a first buttress end portion to a first end of the buttress,
 (B) a second end slit extending longitudinally through a second buttress end portion to a second end of the buttress, and
 (C) an intermediate slit extending longitudinally through an intermediate buttress portion, wherein the intermediate slit is longitudinally spaced apart from each of the first end slit and the second end slit without any intervening slits therebetween,
 wherein the intermediate slit is longitudinally spaced apart from the first end slit by a different distance than from the second end slit.

18. The buttress applier cartridge assembly of claim 17, wherein the first end slit comprises a proximal end slit that extends longitudinally through a proximal buttress end portion to a proximal end of the buttress, wherein the second end slit comprises a distal end slit that extends longitudinally through a distal buttress end portion to a distal end of the buttress, wherein the intermediate slit is spaced apart from the proximal end slit by a greater distance than from the distal end slit.

19. A buttress applier cartridge assembly, comprising:
 (a) a buttress assembly configured to be positioned on a platform and exposed in a gap of a housing, wherein the buttress assembly includes:
  (i) a buttress configured to be received against tissue and support a staple formed therein, wherein the buttress includes:
   (A) a first outer film layer,
   (B) a second outer film layer, and
   (C) a core layer laminated between the first and second outer film layers; and
  (ii) an adhesive layer on the first outer film layer configured to be exposed in the gap of the housing and further configured to releasably adhere the buttress against an end effector of a surgical stapler, wherein the adhesive layer includes a plurality of elongate bead portions that extend parallel to a longitudinal centerline of the buttress assembly, wherein the adhesive bead layer encloses at least one region of the buttress that is free of adhesive,
  wherein each of the first and second outer film layers, the core layer, and the adhesive layer is configured to be absorbed by tissue.

20. The buttress applier cartridge assembly of claim 19, wherein the at least one region of the buttress comprises a plurality of regions.

\* \* \* \* \*